(12) United States Patent
Zhai et al.

(10) Patent No.: US 12,280,079 B2
(45) Date of Patent: Apr. 22, 2025

(54) **STRAIN OF *LACTOBACILLUS CRISPATUS* CAPABLE OF PREVENTING AND/OR TREATING *HELICOBACTER PYLORI* INFECTION**

(71) Applicant: Jiangnan University, Wuxi (CN)

(72) Inventors: Qixiao Zhai, Wuxi (CN); Wei Chen, Wuxi (CN); Meiyi Zhang, Wuxi (CN); Leilei Yu, Wuxi (CN); Fengwei Tian, Wuxi (CN); Shunhe Wang, Wuxi (CN); Jianxin Zhao, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 463 days.

(21) Appl. No.: 17/709,527

(22) Filed: Mar. 31, 2022

(65) Prior Publication Data

US 2022/0218769 A1   Jul. 14, 2022

Related U.S. Application Data

(63) Continuation of application No. PCT/CN2021/095766, filed on May 25, 2021.

(30) Foreign Application Priority Data

May 29, 2020 (CN) .......................... 202010479611.4

(51) Int. Cl.
| | |
|---|---|
| *A61K 35/747* | (2015.01) |
| *A61K 9/20* | (2006.01) |
| *A61K 47/69* | (2017.01) |
| *A61P 31/04* | (2006.01) |
| *C12N 1/20* | (2006.01) |
| *C12R 1/225* | (2006.01) |

(52) U.S. Cl.
CPC .............. *A61K 35/747* (2013.01); *A61K 9/20* (2013.01); *A61K 47/6911* (2017.08); *A61K 47/6925* (2017.08); *A61K 47/6929* (2017.08); *A61P 31/04* (2018.01); *C12N 1/205* (2021.05); *C12R 2001/225* (2021.05)

(58) Field of Classification Search
None
See application file for complete search history.

(56) References Cited

U.S. PATENT DOCUMENTS

2014/0072543 A1*   3/2014   Mogna .................. A23L 33/135
435/252.9

* cited by examiner

*Primary Examiner* — Vera Afremova
(74) *Attorney, Agent, or Firm* — IPRO, PLLC

(57) ABSTRACT

The disclosure discloses a strain of *Lactobacillus crispatus* capable of preventing and/or treating *Helicobacter pylori* infection, and belongs to the technical fields of microorganisms and medicine. The disclosure provides a strain of *Lactobacillus crispatus* CCFM1118. The *Lactobacillus crispatus* CCFM1118 can inhibit *Helicobacter pylori*, specifically embodied in that: (1) the diameter of an inhibition zone of supernatant of the *Lactobacillus crispatus* CCFM1118 on *Helicobacter pylori* can reach 13.14 mm; and (2) the *Lactobacillus crispatus* CCFM1118 can significantly reduce the adhesion of *Helicobacter pylori* to AGS cells. Therefore, the *Lactobacillus crispatus* CCFM1118 has great application prospects in inhibiting *Helicobacter pylori* (not for the purposes of disease diagnosis and treatment) and preparing *Helicobacter pylori* inhibitors.

11 Claims, 2 Drawing Sheets
Specification includes a Sequence Listing.

SEQUENCE LISTING

```
<160> NUMBER OF SEQ ID NOS: 1

<210> SEQ ID NO 1
<211> LENGTH: 1165
<212> TYPE: DNA
<213> ORGANISM: Lactobacillus crispatus
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (1082)..(1082)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1154)..(1158)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t

<400> SEQUENCE: 1
gagnnnnnnt ncnngcctta dacggctcct tcccgaaggt taggccaccg gctttgggca      60
ttgcagactc ccatggtgtg acgggcggtg tgtacaaggc ccgggaacgt attcaccgcg     120
gcgtgctgat ccgcgattac tagcgattcc agcttcgtgc agtcgagttg cagactgcag     180
tccgaactga gaacagcttt cagagattcg cttgccttcg caggctcgct tctcgttgta     240
ctgcccattg tagcacgtgt gtagcccagg tcataagggg catgatgact tgacgtcatc     300
cccaccttcc tccggtttgt caccggcagt ctcattagag tgcccaactt aatgctggca     360
actaataaca agggttgcgc tcgttgcggg acttaaccca acatctcacg acacgagctg     420
```

```
acgacagcca tgcaccacct gtcttagcgt ccccgaaggg aactttgtat ctctacaaat      480
ggcactagat gtcaagacct ggtaaggttc ttcgcgttgc ttcgaattaa accacatgct      540
ccaccgcttg tgcgggcccc cgtcaattcc tttgagtttc aaccttgcgg tcgtactccc      600
caggcggagt gcttaatgcg ttagctacag cactgagagg cggaaacctc ccaacactta      660
gcactcatcg tttacggcat ggactaccag ggtatctaat cctgttcgct acccatgctt      720
tcgagcctca gcgtcagttg cagaccagag agccgccttc gccactggtg ttcttccata      780
tatctacgca ttccaccgct acacatggag ttccactctc ctcttctgca ctcaagaaaa      840
acagtttccg atgcagttcc tcggttaagc cgagggcttt cacatcagac ttattcttcc      900
gcctgcgctc gctttacgcc caataaatcc ggacaacgct tgccacctac gtattaccgc      960
ggctgctggc acgtagttag ccgtgactt ctggttgatt accgtcaaat aaaggccagt     1020
tactacctct atccttcttc accaacaaca gagctttacg atccgaaaac ctctcactca     1080
cncggcntgc tccatcagac ttgcgtcatt gtggaagatt ccctactgct gcctccgtag     1140
aagttggggc ngtnnnnnct cagnn                                            1165
```

STRAIN OF *LACTOBACILLUS CRISPATUS* CAPABLE OF PREVENTING AND/OR TREATING *HELICOBACTER PYLORI* INFECTION

TECHNICAL FIELD

The disclosure relates to a strain of *Lactobacillus crispatus* capable of preventing and/or treating *Helicobacter pylori* infection, and belongs to the technical fields of microorganisms and medicine.

BACKGROUND

*Helicobacter pylori* (Hp) is an S-shaped or curved gram-negative bacterium. In 1982, Barry J. Marshall and J. Robin Warren isolated and cultured *Helicobacter pylori* from human gastric mucosal specimens, and successfully revealed its potential pathogenic mechanism. Both Barry J. Marshall and J. Robin Warren won the 2005 Nobel Prize in Physiology or Medicine. In 1994, *Helicobacter pylori* was designated as a Class I carcinogen by the World Health Organization. At the present stage, the global infection rate of *Helicobacter pylori* has reached about 50%, and the infection rate of *Helicobacter pylori* in developing countries is higher than that in developed countries.

*Helicobacter pylori* infection is a long-term and chronic process. After infection, *Helicobacter pylori* is generally difficult to clear spontaneously by the human body, leading to lifelong infection. *Helicobacter pylori* will disappear automatically in the human body unless the human body undergoes eradication treatment, or severe intestinal metaplasia occurs in the human gastric mucosa and makes it difficult for bacteria to colonize. Studies have shown that long-term infection of *Helicobacter pylori* can cause chronic gastritis, and as the degree of infection deepens and the condition worsens, some patients will develop duodenal ulcers and even gastric cancer. The amount of colonization of *Helicobacter pylori* in the stomach directly affects the development of gastric disease. Generally, the higher the density of *Helicobacter pylori* in a patient, the higher the possibility and degree of the gastric disease. Therefore, inhibiting the growth of *Helicobacter pylori* and reducing its colonization density in patients are of great significance for the prevention and/or treatment of gastric lesions caused by *Helicobacter pylori* infection.

At present, triple or quadruple therapies combined with antibiotics are mainly adopted to inhibit the growth of *Helicobacter pylori* and reduce its colonization density in patients. However, due to frequent use of antibiotics in the above treatment methods, the drug resistance of *Helicobacter pylori* is likely to increase. In addition, in the process of treating patients with the above treatment methods, patients often have serious adverse reactions (such as abdominal pain, nausea, and diarrhea), resulting in a decrease in the effective rate of treatment, and the treatment effect is often not as good as expected.

Therefore, there is still a need for a drug or treatment that will not increase the drug resistance of *Helicobacter pylori*, and at the same time, will not cause adverse reactions in patients during the treatment process, so as to improve the clinical treatment effect of *Helicobacter pylori*.

SUMMARY

Technical Problem

The technical problem to be solved by the disclosure is to provide a strain of *Lactobacillus crispatus* capable of preventing and/or treating *Helicobacter pylori* infection.

Technical Solution

To solve the above problems, the disclosure provides a strain of *Lactobacillus crispatus* CCFM1118. The *Lactobacillus crispatus* CCFM1118 is preserved in the Guangdong Microbial Culture Collection Center, the preservation number is GDMCC NO: 61012, and the preservation date is May 6, 2020.

The *Lactobacillus crispatus* CCFM1118 is derived from a fresh feces sample from an 8-year-old child in Changshou Village, Jiazhuan Township, Bama County, Guangxi Province. The strain was sequenced and analyzed, and the 16S rDNA sequence of the strain is shown in SEQ ID NO. 1. The sequence obtained by sequencing was compared in GeneBank. The result shows that the strain is *Lactobacillus crispatus*, named *Lactobacillus crispatus* CCFM1118.

The colony of the *Lactobacillus crispatus* CCFM1118 on an MRS solid medium is milky white semi-circular convex, smooth and moist in surface, and neat in edges.

The disclosure also provides application of the above *Lactobacillus crispatus* CCFM1118 in inhibiting *Helicobacter pylori* not for the purposes of disease diagnosis and treatment.

The disclosure further provides a *Helicobacter pylori* inhibitor, containing the above *Lactobacillus crispatus* CCFM1118.

The disclosure further provides application of the above *Lactobacillus crispatus* CCFM1118 in the preparation of a product for preventing and/or treating *Helicobacter pylori* infection.

In one example of the disclosure, in the product, a live count of the above *Lactobacillus crispatus* CCFM1118 is not less than $5 \times 10^9$ CFU/mL or $5 \times 10^9$ CFU/g.

In one example of the disclosure, the product includes food or medicine.

In one example of the disclosure, the medicine contains the above *Lactobacillus crispatus* CCFM1118, a drug carrier and/or a pharmaceutical excipient.

In one example of the disclosure, the drug carrier includes microcapsules, microspheres, nanoparticles and/or liposomes.

In one example of the disclosure, the pharmaceutical excipient includes excipients and/or additives.

In one example of the disclosure, the excipients include binders, fillers, disintegrants and/or lubricants.

In one example of the disclosure, the additives include solubilizers, co-solvents, latent solvents and/or preservatives.

In one example of the disclosure, a preparation of the medicine is powders, granules, capsules, tablets, pills or oral liquids.

In one example of the disclosure, the food is a health food; or the food is a dairy product, a bean product, or a fruit and vegetable product produced using a starter containing the above *Lactobacillus crispatus* CCFM1118; or the food is a beverage or a snack food containing the above *Lactobacillus crispatus* CCFM1118.

In one example of the disclosure, the preparation method of the starter is: inoculating the above-mentioned *Lactoba-* cillus crispatus CCFM1118 into the culture medium according to the inoculation amount of 2-4% of the total mass of the culture medium, and culturing the *Lactobacillus crispatus* CCFM1118 at 37° C. for 18 h to obtain a culture solution; centrifuging the culture solution to obtain bacterial cells; washing the bacterial cells with physiological saline for 3 times and resuspending the bacterial cells with a freeze-drying protectant to obtain a resuspension; and freeze-drying the resuspension by vacuum freezing to obtain the starter.

In one example of the disclosure, a mass ratio of the freeze-drying protectant to the bacterial cells is 2:1.

In one example of the disclosure, the freeze-drying protectant contains skimmed milk powder with a concentration of 130 g/L.

In one example of the disclosure, the medium contains the following components (calculated as a percentage of the total mass of the medium): 87.7% water, 10% skim milk, 0.5% glucose, 1.5% tryptone, 0.3% yeast extract.

In one example of the disclosure, the pH value of the medium is 6.8.

The disclosure further provides a product for preventing and/or treating *Helicobacter pylori* infection, the product containing the *Lactobacillus crispatus* CCFM1118.

In one example of the disclosure, in the product, a live count of the above *Lactobacillus crispatus* CCFM1118 is not less than $5 \times 10^9$ CFU/mL or $5 \times 10^9$ CFU/g.

In one example of the disclosure, the product includes food or medicine.

In one example of the disclosure, the medicine contains the above *Lactobacillus crispatus* CCFM1118, a drug carrier and/or a pharmaceutical excipient.

In one example of the disclosure, the drug carrier includes microcapsules, microspheres, nanoparticles and/or liposomes.

In one example of the disclosure, the pharmaceutical excipient includes excipients and/or additives.

In one example of the disclosure, the excipients include binders, fillers, disintegrants and/or lubricants.

In one example of the disclosure, the additives include solubilizers, co-solvents, latent solvents and/or preservatives.

In one example of the disclosure, a preparation of the medicine is powders, granules, capsules, tablets, pills or oral liquids.

In one example of the disclosure, the food is a health food; or the food is a dairy product, a bean product, or a fruit and vegetable product produced using a starter containing the above *Lactobacillus crispatus* CCFM1118; or the food is a beverage or a snack food containing the above *actobacillus crispatus* CCFM1118.

In one example of the disclosure, the preparation method of the starter is: inoculate the above-mentioned *Lactobacillus crispatus* CCFM1118 into the culture medium, and the inoculation amount of the *Lactobacillus crispatus* CCFM1118 is: 2-4% of the total mass of the culture medium is inoculated, and culturing the bacteria at 37° C. for 18 h to obtain a culture solution; centrifuging the culture solution to obtain bacterial cells; washing the bacterial cells with physiological saline 3 times and resuspending the bacterial cells with a freeze-drying protectant to obtain a resuspension; and freeze-drying the resuspension by vacuum freezing to obtain the starter.

In one example of the disclosure, a mass ratio of the freeze-drying protectant to the bacterial cells is 2:1.

In one example of the disclosure, the freeze-drying protectant contains skimmed milk powder with a concentration of 130 g/L.

In one example of the disclosure, The medium contains the following components (calculated as a percentage of the total mass of the medium): 87.7% water, 10% skim milk, 0.5% glucose, 1.5% tryptone, 0.3% yeast extract.

In one example of the disclosure, the pH value of the medium is 6.8.

Beneficial Effects:

1. The disclosure provides a strain of *Lactobacillus crispatus* CCFM1118. The *Lactobacillus crispatus* CCFM1118 can inhibit *Helicobacter pylori*, specifically embodied in that:
   (1) the diameter of an inhibition zone of supernatant of the *Lactobacillus crispatus* CCFM1118 on *Helicobacter pylori* can reach 13.14 mm; and
   (2) the *Lactobacillus crispatus* CCFM1118 can significantly reduce the adhesion of *Helicobacter pylori* to AGS cells.

Therefore, the *Lactobacillus crispatus* CCFM1118 has great application prospects in inhibiting *Helicobacter pylori* (not for the purposes of disease diagnosis and treatment) and preparing *Helicobacter pylori* inhibitors.

2. The disclosure provides a strain of *Lactobacillus crispatus* CCFM1118, and the *Lactobacillus crispatus* CCFM1118 can prevent and/or treat *Helicobacter pylori* infection, specifically embodied in that:
   (1) the *Lactobacillus crispatus* CCFM1118 can significantly reduce the colonization amount of *Helicobacter pylori* in patients with *Helicobacter pylori* infection; and
   (2) the *Lactobacillus crispatus* CCFM1118 can significantly reduce the degree of *Helicobacter pylori* infection in patients with *Helicobacter pylori* infection.

Therefore, the *Lactobacillus crispatus* CCFM1118 has great application prospects in the preparation of products (such as food or medicine) for preventing and/or treating *Helicobacter pylori* infection.

3. *Lactobacillus crispatus* is a kind of probiotics, and has been included in the "List of Bacteria that Can Be Used in Food" issued by the Ministry of Health of China. Therefore, the product of the disclosure with the *Lactobacillus crispatus* CCFM1118 as an active ingredient cannot cause *Helicobacter pylori* to develop drug resistance, and at the same time, cannot cause adverse reactions in patients during the treatment process.

Preservation of Biological Material

A strain of *Lactobacillus crispatus* CCFM1118, taxonomically named *Lactobacillus crispatus*, was preserved at the Guangdong Microbial Culture Collection Center on May 6, 2020, the preservation number is GDMCC NO. 61012, and the preservation address is 5th Floor, Building 59, Grand Courtyard 100, Xianlie Middle Road, Guangzhou.

DETAILED DESCRIPTION

Figure 1:
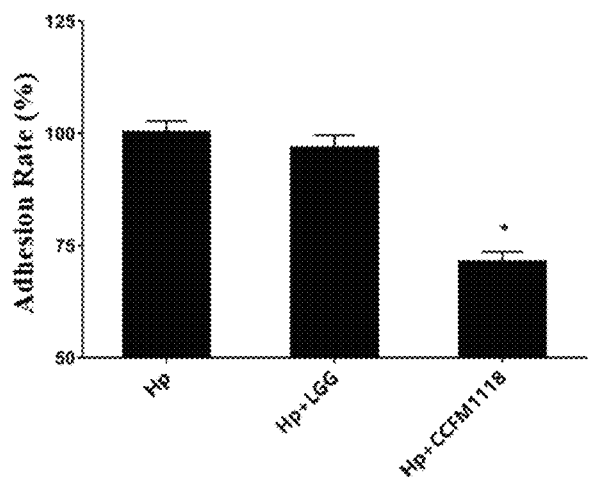
FIG. 1 shows the adhesion rate of *Helicobacter pylori* to AGS cells in different groups.

The *Helicobacter pylori* involved in the following examples is *Helicobacter pylori* SS1 from the National Type Culture Collection (NTCC). The *Lactobacillus rhamnosus* L. GG involved in the following examples is derived from the American Type Culture Collection (ATCC), and the preservation number is ATCC 53103. The F12 liquid medium and fetal calf serum involved in the following examples were purchased from Gibco, USA. The NaCl involved in the following examples was purchased from Sinopharm. The phenol red and urea involved in the following examples were purchased from Macklin. The Columbia medium involved in the following examples was purchased from OXOID, the United Kingdom. The sterile defibered sheep blood involved in the following examples was purchased from Hangzhou Sinry Bio-engineering Co., Ltd. The BHI liquid medium involved in the following examples was purchased from Qingdao Hope Bio-Technology Company.

Media involved in the following examples are as follows:

MRS solid medium: Peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7H_2O$ 0.1 g/L, $MnSO_4$ 0.05 g/L, Tween 80 1 mL/L, agar 20 g/L, and cysteine hydrochloride 0.5 g/L.

MRS liquid medium: Peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7H_2O$ 0.1 g/L, $MnSO_4$ 0.05 g/L, Tween 80 1 mL/L, and cysteine hydrochloride 0.5 g/L.

Detection methods involved in the following examples are as follows:

Detection method of live count: National standard "GB 4789.35-2016 National Food Safety Standard, Food Microbiology Detection, Lactic Acid Bacteria Detection".

A preparation method of *Helicobacter pylori* cells involved in the following examples is as follows:

*Helicobacter pylori* is streaked on a Columbia blood agar medium, and cultured in a three-gas incubator (85% $N_2$, 10% $CO_2$ and 5% $O_2$) at 37° C. for 3 days to obtain a single colony. The single colony is picked and inoculated in a BHI medium containing 5% (v/v) fetal calf serum, and cultured in a three-gas incubator (85% $N_2$, 10% $CO_2$ and 5% $O_2$) at 37° C. for 4 days to obtain a seed solution. The seed solution is inoculated in BHI liquid medium at the inoculation amount of 2% (v/v), and the seed solution is cultured in a three-gas incubator (85% $N_2$, 10% $CO_2$ and 5% $O_2$) at 37° C. for 4 days to obtain a *Helicobacter pylori* bacterial solution. The *Helicobacter pylori* bacterial solution is centrifuged at 8,000 g for 10 min and filtered to obtain *Helicobacter pylori* bacterial cells.

The Columbia blood agar medium is prepared as follows: 39 g of Columbia medium solid powder is dissolved in 1 L of water. The solution is sterilized at 121° C. for 15 min. After cooling to 55° C. to 60° C., 7.5% (v/v) sterile defibered sheep blood is added, and the solution is mixed uniformly and poured into a plate.

A preparation method of *Lactobacillus rhamnosus* cells involved in the following examples is as follows:

*Lactobacillus rhamnosus* is streaked on an MRS solid medium and cultured at 37° C. for 48 h to obtain a single colony. The single colony is picked and inoculated in the MRS liquid medium, and cultured at 37° C. for 18 h for activation, and activated for two consecutive generations to obtain an activation solution. The activation solution is inoculated in MRS liquid medium at an inoculation amount of 2% (v/v), and cultured at 37° C. for 18 h to obtain a bacterial solution. The bacterial solution is centrifuged at 8,000 g for 10 min and filtered to obtain *Lactobacillus rhamnosus* bacterial cells.

A preparation method of *Lactobacillus crispatus* cells involved in the following examples is as follows:

*Lactobacillus crispatus* is streaked on an MRS solid medium and cultured at 37° C. for 48 h to obtain a single colony. The single colony is picked and inoculated in the MRS liquid medium, and the single colony is cultured at 37° C. for 18 h for activation, and activated for two consecutive generations to obtain an activation solution. The activation solution is inoculated in MRS liquid medium at an inoculation amount of 2% (v/v), and cultured at 37° C. for 18 h to obtain a bacterial solution. The bacterial solution is centrifuged at 8,000 g for 10 min and filtered to obtain *Lactobacillus crispatus* bacterial cells.

EXAMPLE 1

Screening and Identification of *Lactobacillus crispatus*

1. Screening

Fresh feces of healthy humans from Kunshan, Jiangsu was taken as a sample. The sample was pretreated, and the pretreated sample was stored in a refrigerator at −80° C. in about 30% glycerol. After the sample was taken out and thawed, the sample was mixed uniformly. 0.5 mL of the sample was pipetted and added to 4.5 mL of 0.9% physiological saline and subjected to gradient dilution. An appropriate gradient dilution was selected and spread on an MRS solid medium. The MRS solid medium was cultured at 37° C. for 48 h. Typical colonies were picked and streaked on an MRS plate for performing purification. A single colony was picked and transferred to an MRS liquid medium for performing culture and enrichment to obtain the strain CCFM1118 (the original number of the strain is G14-5M), and the strain was preserved with 30% glycerol in a tube.

2. Identification

The genome of the CCFM1118 was extracted, and the 16S rDNA of the CCFM1118 was amplified and sequenced (completed by Sangon Biotech (Shanghai) Co., Ltd.). By sequencing analysis, the 16S rDNA sequence of the strain is shown in SEQ ID NO. 1. The sequence was compared in GenBank, and the result showed that the strain was *Lactobacillus crispatus*, named *Lactobacillus crispatus* CCFM1118.

EXAMPLE 2

Culture of *Lactobacillus crispatus*

*Lactobacillus crispatus* CCFM1118 was inoculated in MRS solid medium and cultured at 37° C. for 48 h. Then the colony was observed, and the bacterial cells were observed under a microscope. It was found that the colony was milky white semi-circular convex, smooth and moist in surface, and neat in edges.

*Lactobacillus crispatus* CCFM1118 was inoculated in MRS liquid medium and cultured at 37° C. for 48 h. During the culture process, the pH value of the culture solution was measured with a pH meter at intervals, and it was found that the *Lactobacillus crispatus* CCFM1118 could produce acid during the culture process.

*Lactobacillus crispatus* CCFM1118 was inoculated in MRS liquid medium and cultured at 10-50° C. for 48 h. During the culture process, the $OD_{600}$ of the culture solution was measured with a microplate reader at intervals, and it was found that the *Lactobacillus crispatus* CCFM1118 grew best at 30-37° C. and reached a stable growth period after being cultured for 18-24 h.

EXAMPLE 3

Inhibition Effect of *Lactobacillus crispatus* on *Helicobacter pylori*

An MRS liquid medium was used as a negative control. *Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in MRS liquid medium at an inoculation amount of 2% (v/v) and cultured at 37° C. for 18 h to obtain a bacterial solution. The bacterial solution was centrifuged at 8,000 g for 10 min and filtered with a 0.22 μm sterile filter membrane to obtain supernatant. The diameter of the inhibition zone of the supernatant of *Lactobacillus crispatus* CCFM1118 on *Helicobacter pylori* was measured by the Oxford cup method to indicate the effect of inhibiting the growth of *Helicobacter pylori*. The measurement results are shown in Table 1. (For details of the Oxford cup method, please refer to the literature: Zhang Tingting, Zhai Qixiao, Jin Xing, et. al. Screening and characterization of lactic acid bacteria with antagonistic activities against *Campylobacter jejuni* from chicken manure. Microbiology China, 2017, (44): 118-125).

It can be seen from Table 1 that the MRS liquid medium has no inhibition zone on *Helicobacter pylori*, while the diameter of the inhibition zone of the *Lactobacillus crispatus* CCFM1118 supernatant on *Helicobacter pylori* can reach 13.14 mm, indicating that the *Lactobacillus crispatus* CCFM1118 can inhibit the growth of *Helicobacter pylori*.

TABLE 1

The diameter of the inhibition zone of *Lactobacillus crispatus* CCFM1118 on *Helicobacter pylori*

| Group | pH | Diameter of inhibition zone (mm) |
| --- | --- | --- |
| Negative control | 6.2 | 0 |
| CCFM1118 | 3.81 | 13.14 ± 1.05 |

EXAMPLE 4

Effect of *Lactobacillus crispatus* on Adhesion of *Helicobacter pylori*

Specific steps are as follows:
(1) Preparation of Resuspension

*Helicobacter pylori* cells were resuspended in an F12 medium to a concentration of $1\times10^7$ CFU/mL to obtain a *Helicobacter pylori* resuspension. *Lactobacillus rhamnosus* L. GG cells were resuspended in an F12 medium to a concentration of $1\times10^7$ CFU/mL to obtain a *Lactobacillus rhamnosus* L. GG resuspension. *Lactobacillus crispatus* CCFM1118 cells were resuspended in an F12 medium to a concentration of $1\times10^7$ CFU/mL to obtain a *Lactobacillus crispatus* CCFM1118 resuspension.

(2) Preparation of *Helicobacter pylori*-Infected AGS Cells

AGS cells were resuspended in an F12 medium containing 5% (v/v) fetal calf serum and then added to a 96-well plate ($2\times10^4$ cells/well), and cultured at 37° C. in 5% $CO_2$ for 12-16 h Until the AGS cells were in an adherent state, the AGS cells were washed 3 times with PBS to remove dead cells. The *Helicobacter pylori* resuspension was added to the washed AGS cells, and cultured in an incubator at 37° C. in 5% $CO_2$ for 2 h. The AGS cells were washed with a PBS solution 3 times to remove unabsorbed *Helicobacter pylori* and obtain *Helicobacter pylori*-infected AGS cells.

(3) Use the AGS Cells that were Not Treated with *Lactobacillus rhamnosus* L. GG or *Lactobacillus crispatus* CCFM1118 and Not Infected with *Helicobacter pylori* as a Blank Group

*Helicobacter pylori*-infected AGS cells not treated with *Lactobacillus rhamnosus* L. GG or *Lactobacillus crispatus* CCFM1118 were a model group (Hp group).

*Helicobacter pylori*-infected AGS cells treated with *Lactobacillus rhamnosus* L. GG and *Helicobacter pylori*-infected AGS cells treated with *Lactobacillus crispatus* CCFM1118 were experimental groups, named an Hp+LGG group and an Hp+CCFM1118 group respectively.

0.2 mL of *Lactobacillus rhamnosus* L. GG resuspension or *Lactobacillus crispatus* CCFM1118 resuspension was added to *Helicobacter pylori*-infected AGS cells respectively, and the cells were cultured in an incubator at 37° C. in 5% $CO_2$ for 2 h to obtain *Helicobacter pylori*-infected AGS cells treated with *Lactobacillus rhamnosus* L. GG and *Helicobacter pylori*-infected AGS cells treated with *Lactobacillus crispatus* CCFM1118. After the *Helicobacter pylori*-infected AGS cells treated with *Lactobacillus rhamnosus* L. GG and the *Helicobacter pylori*-infected AGS cells treated with *Lactobacillus crispatus* CCFM1118 were washed with a PBS solution 5 times, 200 μL of urease reagent (9 g/L NaCl, 14 μg/mL phenol red, 20 mM urea, pH 6.8) was added to the *Helicobacter pylori*-infected AGS cells treated with *Lactobacillus rhamnosus* L. GG and the *Helicobacter pylori*-infected AGS cells treated with *Lactobacillus crispatus* CCFM1118 respectively, and the cells were cultured in an incubator at 37° C. in 5% $CO_2$ for 2 h to obtain culture solutions.

The absorbance of the culture solutions of different groups was measured at a wavelength of 550 nm by using a microplate reader. The adhesion rate determined by subtracting the absorbance of the blank group from the absorbance of the model group is 100%. The relative adhesion rate was the value obtained by the absorbance of the remaining groups minus the absorbance of the blank group versus the value of obtained by the absorbance of the model group minus the absorbance of the blank group. The measurement results are shown in FIG. 1.

It can be seen from FIG. 1 that after treatment with *Lactobacillus crispatus* CCFM1118, the adhesion rate of *Helicobacter pylori* to the AGS cells decreased significantly, from 100% in the model group (Hp group) to about 70%. However, *Lactobacillus rhamnosus* L. GG did not significantly reduce the adhesion rate of *Helicobacter pylori* to the AGS cells, and the adhesion rate of *Helicobacter pylori* hardly changed. The result shows that *Lactobacillus crispatus* CCFM1118 can effectively reduce the adhesion of *Helicobacter pylori* to the AGS cells.

EXAMPLE 5

Effect of *Lactobacillus crispatus* on Colonization Amount and Clearance Rate of *Helicobacter pylori* in *Helicobacter pylori* Positive Patients

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation was inoculated in the medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1\times10^{10}$ CFU/mL to obtain a bacterial suspension. The bacterial suspension was pre-cultured at 37° C. for 60 min and then freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

30 *Helicobacter pylori*-positive infected patients (Table 2 shows the population distribution of recruited patients, and the difference in baseline conditions between the two groups of people is of no statistical significance) were recruited. The 30 *Helicobacter pylori*-positive infected patients were randomly divided into 2 groups, including 13 in a placebo group (Placebo) and 17 in a *Lactobacillus crispatus* CCFM1118 group (CCFM1118).

The placebo group (Placebo) took placebo twice a day, and the *Lactobacillus crispatus* CCFM1118 group took the bacterial powder twice a day. The whole experiment period is 1 month (the placebo and the *Lactobacillus crispatus* bacterial powder contain different components, but the appearances and packaging of the products are the same without significant difference).

The 14C-urea breath test values of the *Helicobacter pylori*-positive infected patients in the placebo group and the *Lactobacillus crispatus* CCFM1118 group were measured by a 14C-urea breath test reagent bag and a tester before and after the experiment respectively, to evaluate the colonization amount and clearance rate of *Helicobacter pylori* in the patients. The measurement results are shown in FIG. 2 and Table 3.

The evaluation criterion for the amount of colonization of *Helicobacter pylori* is: The decrease in the 14C-urea breath test values of *Helicobacter pylori*-positive infected patients after the end of the experiment compared with the 14C-urea breath test values of *Helicobacter pylori*-positive infected patients before the start of the experiment.

The evaluation criterion for the clearance rate of *Helicobacter pylori* is as follows: The threshold of the clinical 14C-urea breath test value is 100, that is, if the 14C-urea breath test value is greater than or equal to 100, the infection of *Helicobacter pylori* is positive, and if the 14C-urea breath test value is lower than 100, the infection of *Helicobacter pylori* is negative. After the end of the experiment, whether the *Helicobacter pylori*-positive infected patient becomes negative is used to evaluate the increase of the clearance rate of *Helicobacter pylori*-positive infected patients.

Figure 2:
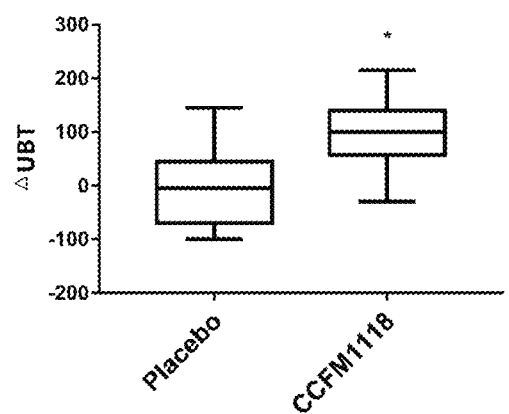
FIG. 2 shows changes in 14C-urea breath test values of *Helicobacter pylori*-positive patients in different groups.

It can be seen from FIG. 2 that after the end of the experiment, the 14C-urea breath test values of the *Helicobacter pylori*-positive infected patients in the placebo group (Placebo) were almost the same as before the start of the experiment. However, the 14C-urea breath test values of the *Helicobacter pylori*-positive infected patients in the *Lactobacillus crispatus* CCFM1118 group (CCFM1118) decreased by about 100 compared with that before the start of the experiment, and the two groups have a significant difference. The result indicates that the *Lactobacillus crispatus* CCFM1118 can significantly reduce the amount of colonization of *Helicobacter pylori* in *Helicobacter pylori*-infected patients.

It can be seen from Table 3 that after the end of the experiment, 2 out of 13 people in the placebo group (Placebo) became *Helicobacter pylori* negative, and the negative rate was 15.38%. Of the 17 people in the *Lactobacillus crispatus* CCFM1118 group, 12 people became *Helicobacter pylori* negative, and the negative rate was as high as 70.59%, which was significantly higher than that of the placebo group. The result indicates that the *Lactobacillus crispatus* CCFM1118 can significantly reduce the *Helicobacter pylori* infection degree in the *Helicobacter pylori*-infected patients.

TABLE 2

Population distribution of recruited *Helicobacter pylori*-positive infected patients

| Group | Number of people (N) | Age | Male/female | Drinker/non-drinker | Smoker/non-smoker |
|---|---|---|---|---|---|
| Placebo | 13 | 48.15 ± 3.70 | 2/11 | 1/12 | 0/13 |
| CCFM1118 | 17 | 46.53 ± 2.79 | 6/11 | 4/13 | 3/14 |

TABLE 3

Infection degrees of *Helicobacter pylori*-positive patients in different groups

| Group | Number of people (N) | Positive n | Negative n | Negative rate (%) |
|---|---|---|---|---|
| Placebo | 13 | 11 | 2 | 15.38 |
| CCFM1118 | 17 | 5 | 12 | 70.59* |

Note:
*indicates a significant difference compared with the placebo group ($p < 0.05$).

EXAMPLE 6

Application of *Lactobacillus crispatus*

*Lactobacillus crispatus* CCFM1118 can be used to prepare bacterial powder. The specific preparation process of the bacterial powder is as follows:

*Lactobacillus crispatus* CCFM1118 was streaked on an MRS solid medium and cultured at 37° C. for 48 h to obtain a single colony. The single colony was picked and inoculated in MRS liquid medium was inoculated with the single colon, and cultured at 37° C. for 18 h for activation, and activated for two consecutive generations to obtain an activation solution. The activation solution was inoculated in medium at an inoculation amount of 2% (v/v) and cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1\times10^{10}$ CFU/mL to obtain a bacterial suspension. The bacterial suspension was pre-cultured at 37° C. for 60 min and then freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

2 g of *Lactobacillus crispatus* CCFM1118 bacterial powder was accurately weighed and dissolved in 10 mL of sterile physiological saline to obtain an original bacterial suspension. 0.5 mL of the original bacterial suspension was taken and added to 4.5 mL of sterile physiological saline, and the solution was uniformly mixed. At this time, the original bacterial suspension is diluted 10 times and recorded as "n=10". 0.5 mL of the diluted bacterial suspension was taken and added to 4.5 mL of sterile physiological saline. At this time, the original bacterial suspension is diluted 100 times and recorded as "n=$10^2$". By analogy, the original bacterial suspension was diluted to $1.0 \times 10^8$ times. 0.1 mL of the bacterial suspensions with dilution multiples of $1.0 \times 10^6$ (n=$10^6$), $1.0 \times 10^7$ (n=$10^7$) and $1.0 \times 10^8$ (n=$10^8$) were taken and inoculated into MRS solid medium, and put the medium upside down in an anaerobic box. The bacterial suspensions were cultured in an anaerobic box at 37° C. for 2 d to 3 d, and the live bacteria were counted. The measurement was performed once a week for one month to determine the storage stability of the *Lactobacillus crispatus* CCFM1118 bacterial powder. The measurement results are shown in FIG. 3.

Figure 3:
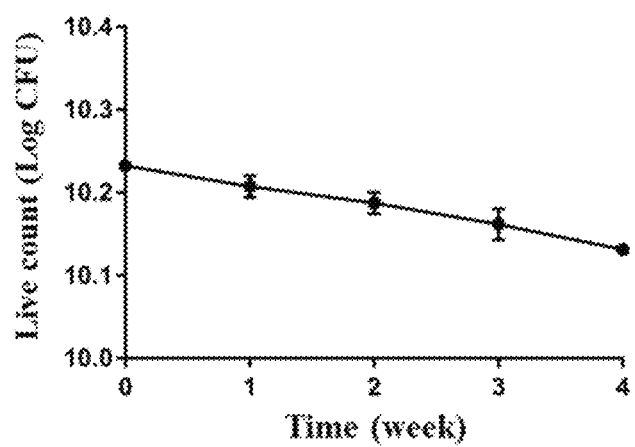
FIG. 3 shows the effect of storage time on the live count of *Lactobacillus crispatus* CCFM1118 bacterial powder.

It can be seen from FIG. 3 that the initial live count of the *Lactobacillus crispatus* CCFM1118 bacterial powder was higher than $10^{10}$ CFU/bag, and met the product specifications. During storage for one month, the live count of the *Lactobacillus crispatus* CCFM1118 bacterial powder did not decrease significantly compared with the initial period, and the live count was always higher than $10^{10}$ CFU/bag, indicating that the performance of the *Lactobacillus crispatus* CCFM1118 bacterial powder is relatively stable during the short-term storage of one month.

EXAMPLE 7

Application of *Lactobacillus crispatus*

*Lactobacillus crispatus* CCFM1118 can be used to prepare a capsule product. The specific preparation process of the capsule product is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline for 3 times and then resuspended with a protectant to a concentration of $1 \times 10^{10}$ CFU/mL to obtain a bacterial suspension. The bacterial suspension was added to a sodium alginate solution with a concentration of 30 g/L to a concentration of $2 \times 10^9$ CFU/mL, and then the solution was fully stirred to make the cells of *Lactobacillus crispatus* CCFM1118 evenly dispersed in the sodium alginate solution to obtain a mixed solution. The mixed solution was squeezed into a calcium chloride solution with a concentration of 20 g/L to form colloidal particles. After the formed colloidal particles were statically solidified for 30 min, the colloidal particles were filtered and collected. The collected colloidal particles were freeze-dried for 48 h to obtain a powder. Medicinal capsules were filled with the powder to obtain a capsule product.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

EXAMPLE 8

Application of *Lactobacillus crispatus*

*Lactobacillus crispatus* CCFM1118 can be used to prepare tablets. The specific preparation process of the tablets is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1 \times 10^{10}$ CFU/mL to obtain a bacterial suspension. The bacterial suspension was pre-cultured at 37° C. for 60 min and then the culture was freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

25.7 parts by weight of the *Lactobacillus crispatus* CCFM1118 bacterial powder, 55.0 parts by weight of starch, 4.5 parts by weight of a cellulose derivative, 12.0 parts by weight of sodium carboxymethyl starch, 0.8 parts by weight of talc, 1.0 part by weight of sucrose, and 1.0 part by weight of water were weighed to obtain raw materials. The raw materials were mixed to obtain wet granules. The wet granules were compressed using a tablet press of Zhongnan Pharmaceutical Machinery Factory, and then the tablets were dried using a small medicine dryer of Qingzhou Yikang Traditional Chinese Medicine Machinery Co., Ltd. to obtain the tablets.

EXAMPLE 9

Application of *Lactobacillus crispatus*

*Lactobacillus crispatus* CCFM1118 can be used to prepare fermented milk. The specific preparation process of the fermented milk is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in MRS liquid medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

The *Lactobacillus crispatus* CCFM1118 bacterial powder was mixed with a commercial dry powder starter *Lactobacillus bulgaricus* and a commercial dry powder starter *Streptococcus thermophilus* at a mass ratio of 1:1:1 to obtain a starter. Sugar was added to fresh milk to a concentration of 50 g/L to obtain a mixed solution. The mixed solution was homogenized at 65° C. and 20 MPa, and then heated and sterilized at 95° C. for 5 min to obtain a fermentation raw material. After the fermentation raw material was cooled to 35° C., the the starter was inoculated in the fermentation raw material at an inoculation amount of 0.03% (v/v), and fermentation was performed at 35° C. for 16 h to obtain the fermented milk. After the fermented milk was stood at 42° C. for 4 h for curdling, the fermented milk was refrigerated at 4° C. for 24 h for aging to obtain the fermented milk product.

EXAMPLE 10

Application of *Lactobacillus crispatus*

*Lactobacillus crispatus* CCFM1118 can be used to prepare soybean milk. The specific preparation process of the soybean milk is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in MRS liquid medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

Soybeans were soaked at a temperature of 80° C. for 2 h and then soybean hulls were removed to obtain dehulled soybeans. The dehulled soybeans were drained to remove soaking water and boiling water was added for performing pulping to obtain soybean milk. The soybean milk was kept at a temperature higher than 80° C. for 12 min to obtain cooked soybean milk. The cooked soybean milk was filtered with a 150-mesh screen and centrifugally separated to obtain crude soybean milk. The crude soybean milk was heated to a temperature of 140-150° C. and then quickly introduced into a vacuum cooling chamber and vacuumized, so that off-flavor substances in the crude soybean milk were quickly discharged with water vapor, and the cooked soybean milk was obtained. After the cooked soybean milk was cooled to about 37° C., the *Lactobacillus crispatus* CCFM1118 bacterial powder was added to the cooked soybean milk to a concentration of not less than $1\times10^6$ CFU/mL to obtain the soybean milk (the soybean milk needs to be stored under refrigeration at 4° C.).

EXAMPLE 11

Application of *Lactobacillus crispatus*

*Lactobacillus crispatus* CCFM1118 can be used to prepare a fruit and vegetable beverage. The specific preparation process of the fruit and vegetable beverage is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in MRS liquid medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of $1\times10^{10}$ CFU/mL to obtain a bacterial suspension. The bacterial suspension was pre-cultured at 37° C. for 60 min and then the culture was freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

Fresh fruits and vegetables were washed and squeezed to obtain fruit and vegetable juice. The fruit and vegetable juice was heated and sterilized at a high temperature of 140° C. for 2 seconds to obtain the sterilized fruit and vegetable juice. After the sterilized fruit and vegetable juice was cooled to about 37° C., the *Lactobacillus crispatus* CCFM1118 bacterial powder was added to the sterilized fruit and vegetable juice to a concentration of not less than $1\times10^6$ CFU/mL to obtain the fruit and vegetable beverage (the fruit and vegetable beverage needs to be stored under refrigeration at 4° C.).

EXAMPLE 12

Application of *Lactobacillus crispatus*

*Lactobacillus crispatus* CCFM1118 can be used to prepare a milk beverage. The specific preparation process of the milk beverage is as follows:

*Lactobacillus crispatus* CCFM1118 was streaked on an MRS solid medium and cultured at 37° C. for 48 h to obtain a single colony. The single colony was picked and inoculated in MRS liquid medium, and cultured at 37° C. for 18 h for activation, and activated for two consecutive generations to obtain an activation solution. The activation solution was inoculated in MRS liquid medium at an inoculation amount of 2% (v/v), and cultured at 37° C. for 18 h to obtain a bacterial solution. The bacterial solution was centrifuged at 8,000 g for 10 min to obtain bacterial sludge. The bacterial sludge was washed with physiological saline 3 times and then resuspended with a protectant to a concentration of 1×10$^{10}$ CFU/mL to obtain a bacterial suspension. The bacterial suspension was pre-cultured at 37° C. for 60 min and then the culture was freeze-dried to obtain *Lactobacillus crispatus* CCFM1118 bacterial powder.

The preparation method of the medium is as follows: 10% of enzymatically hydrolyzed skimmed milk, 0.5% of glucose, 1.5% of tryptone and 0.3% of yeast extract were dissolved in water accounting for 87.7% of the total weight of the medium. Then the pH value of the solution was adjusted to 6.8 to obtain the medium.

The components of the protectant include: 130 g/L skimmed milk powder.

The skimmed milk was heated and sterilized at 95° C. for 20 min and then cooled to 4° C. to obtain the raw material. The *Lactobacillus crispatus* CCFM1118 bacterial powder was added to the raw material to a concentration of not less than 1×10$^6$ CFU/mL to obtain the milk beverage (the milk beverage needs to be stored under refrigeration at 4° C.).

Although the disclosure has been disclosed as above in preferred examples, it is not intended to limit the disclosure. Those skilled in the art can make various alterations and modifications without departing from the spirit and scope of the disclosure. Therefore, the protection scope of the disclosure should be defined by the claims.

What is claimed is:

1. A composition consisting of *Lactobacillus crispatus* CCFM1118, a salt, and a protective agent,
    wherein the *Lactobacillus crispatus* CCFM1118 was preserved at the Guangdong Microbial Culture Collection Center on May 6, 2020, with the preservation number of GDMCC NO: 61012, and
    wherein the composition is freeze-dried, and
    wherein the protective agent is skimmed milk.

2. The composition according to claim 1, wherein the *Lactobacillus crispatus* CCFM1118 is present in an amount of not less than $5 \times 10^9$ CFU/mL or $5 \times 10^9$ CFU/g.

3. A product comprising
    the composition of claim 1, and
    wherein the *Lactobacillus crispatus* CCFM1118 is the only bacterial species present in the product,
    wherein the product is food or medicine.

4. The product according to claim 3, wherein the medicine further comprises a drug carrier and/or a pharmaceutical excipient.

5. The product according to claim 4, wherein the medicine is in a form of a powder, granules, capsules, tablets, pills, or is an oral liquid.

6. The product according to claim 5, wherein the drug carrier is in a form of microcapsules, microspheres, nanoparticles, and/or liposomes.

7. The product according to claim 3, wherein the food is a health food.

8. The product according to claim 3, wherein the food is a dairy product, a bean product, or a fruit and vegetable product.

9. The product according to claim 3, wherein the food is a beverage or a snack food.

10. A method of producing the product of claim 8, beginning with a starter, which is produced as follows:
    inoculating *Lactobacillus crispatus* CCFM1118 into a medium at an inoculation amount of 2% to 4% of a total mass of the medium,
    culturing the *Lactobacillus crispatus* CCFM1118 at 37° C. for 18 hours to obtain a culture solution,
    centrifuging the culture solution to obtain *Lactobacillus crispatus* CCFM1118 cells,
    washing the *Lactobacillus crispatus* CCFM1118 cells with physiological saline 3 times,
    resuspending the *Lactobacillus crispatus* CCFM1118 cells with a freeze-drying protectant to obtain a resuspension, and
    freeze-drying the resuspension by vacuum freezing to obtain the starter.

11. The method according to claim 10, wherein a mass ratio of the freeze-drying protectant to the *Lactobacillus crispatus* CCFM1118 cells is 2:1.

* * * * *